United States Patent
Yang et al.

(10) Patent No.: US 11,154,222 B2
(45) Date of Patent: Oct. 26, 2021

(54) METHOD AND SYSTEM FOR DETERMINING DATA ASSOCIATED WITH LOWER LIMB ACTIVITY

(71) Applicant: NATIONAL CHIAO TUNG UNIVERSITY, Hsinchu (TW)

(72) Inventors: Bing-Shiang Yang, Hsinchu (TW); Yu-Tang Wen, Toufen (TW)

(73) Assignee: NATIONAL CHIAO TUNG UNIVERSITY, Hsinchu (TW)

(*) Notice: Subject to any disclaimer, the term of this patent is extended or adjusted under 35 U.S.C. 154(b) by 841 days.

(21) Appl. No.: 15/807,410

(22) Filed: Nov. 8, 2017

(65) Prior Publication Data

US 2018/0256079 A1    Sep. 13, 2018

(30) Foreign Application Priority Data

Mar. 8, 2017    (TW) .................................. 106107500

(51) Int. Cl.
*A61B 5/11*     (2006.01)
*A61B 5/00*     (2006.01)
(Continued)

(52) U.S. Cl.
CPC .......... *A61B 5/1121* (2013.01); *A61B 5/1036* (2013.01); *A61B 5/1107* (2013.01);
(Continued)

(58) Field of Classification Search
None
See application file for complete search history.

(56) References Cited

U.S. PATENT DOCUMENTS

| | | | | |
|---|---|---|---|---|
| 3,831,942 A | * | 8/1974 | Del Mar | A63B 21/015 482/72 |
| 4,141,248 A | * | 2/1979 | Bargenda | A61B 5/221 73/379.07 |

(Continued)

FOREIGN PATENT DOCUMENTS

| TW | I438018 B | 5/2014 |
|---|---|---|
| TW | I444213 B | 7/2014 |
| TW | I455705 B | 10/2014 |

OTHER PUBLICATIONS

David M. Rouffet, EMG normalization to study muscle activation in cycling, 2008, Journal of Electromyography and Kinesiology, 18, pp. 866-878 (Year: 2008).*

(Continued)

*Primary Examiner* — Sean P Dougherty
(74) *Attorney, Agent, or Firm* — Womble Bond Dickinson (US) LLP

(57) ABSTRACT

A method includes steps of: measuring a variation in joint angle of a knee of a cyclist to obtain joint angle data; sensing a torque applied on a crank of a cycle or pedaling force applied to a pedal of the cycle to obtain force data; measuring an angular position of the crank to obtain crank angle data; measuring an electrical potential variation of a measured muscle of the cyclist to generate a measured EMG signal; estimating activation data and joint moment data based on aforementioned data and characteristics data; converting the activation data into estimated EMG signals based on the measured EMG signal and the activation data; and computing a coactivation parameter based on the aforementioned EMG signals.

20 Claims, 7 Drawing Sheets

(51) Int. Cl.

| | | |
|---|---|---|
| *A61F 2/72* | (2006.01) | |
| *A63B 24/00* | (2006.01) | |
| *A61B 5/103* | (2006.01) | |
| *A61B 5/389* | (2021.01) | |
| *A61F 2/70* | (2006.01) | |
| *A61B 5/22* | (2006.01) | |
| *A61F 2/76* | (2006.01) | |
| *A63B 69/16* | (2006.01) | |
| *A61B 5/30* | (2021.01) | |

(52) U.S. Cl.
CPC ............ *A61B 5/1118* (2013.01); *A61B 5/389* (2021.01); *A61B 5/4528* (2013.01); *A61B 5/486* (2013.01); *A61B 5/6828* (2013.01); *A61B 5/6829* (2013.01); *A61B 5/6895* (2013.01); *A61F 2/72* (2013.01); *A63B 24/0062* (2013.01); *A61B 5/1116* (2013.01); *A61B 5/224* (2013.01); *A61B 5/30* (2021.01); *A61B 5/4519* (2013.01); *A61B 2503/10* (2013.01); *A61B 2562/0219* (2013.01); *A61F 2002/701* (2013.01); *A61F 2002/764* (2013.01); *A63B 24/0003* (2013.01); *A63B 2069/167* (2013.01)

(56) References Cited

U.S. PATENT DOCUMENTS

| | | |
|---|---|---|
| 5,476,103 A | 12/1995 | Nahsner |
| 5,758,658 A | 6/1998 | Petragallo |
| 6,666,801 B1 | 12/2003 | Michalow |
| 7,492,268 B2 | 2/2009 | Ferguson et al. |
| 2003/0171190 A1* | 9/2003 | Rice ...................... A63F 13/803 482/57 |
| 2006/0003872 A1* | 1/2006 | Chiles ................... A63B 24/00 482/57 |
| 2011/0118086 A1* | 5/2011 | Radow ............... A63B 24/0062 482/5 |

OTHER PUBLICATIONS

Laura A. Frey-Law, Muscle Coactivation: A Generalized or Localized Motor Control Strategy?, 2013, Muscle Nerve, 48(4), pp. 578-585 (Year: 2013).*

Eleftherios Kellis, Muscle Coactivation Before and After the Impact Phase of Running Following Isokinetic Fatigue, 2011, J Athl Train, 46(1), pp. 11-19 (Year: 2011).*

Shimpei Matsumo, Tatsushi Tokuyasu, Keichi Ohba, "A Study on Postural Optimization for Bicycle Exercise Based on Electromyography," Artif Life Robotics (2009) 14:144-149.

Yeou-Feng Huang, "A Study of Finding Best Relation Between Pedaling Force and Pedaling Speed while Riding a Bicycle," Master Thesis, Dept. of Power Mechanical Engineering, National Tsing Hua University, 2000. (along with an English abstract).

* cited by examiner

Cycling Diagnosis System

| Name: HuangXX | Age: 26 | Height:173 | | Male | | BW: 70 | | Average RPM:90rpm | | | | Date: November |
|---|---|---|---|---|---|---|---|---|---|---|---|---|

Joint Moment (Nm/kg)

| Crank degree | Hip | | | Knee | | Ankle | | |
|---|---|---|---|---|---|---|---|---|
| | Fle/Ext | Abd/add | rot. | Fle/Ext | Inver/ever | Plan/dorsi |
| TDC | -0.04 | 0.22 | 0.57 | -0.15 | 7.41 | -34.30 |
| 45 | -1.24 | 0.13 | -5.79 | -4.98 | 4.68 | -26.65 |
| 60 | -0.96 | 2.98 | -17.47 | -3.42 | 5.47 | -41.06 |
| 90 | -2.02 | 0.43 | -11.27 | 2.18 | 0.85 | -13.66 |
| 120 | -0.33 | -0.32 | 0.65 | -3.12 | 6.28 | -38.10 |
| BDC | -1.97 | -0.50 | 1.67 | -1.42 | 5.84 | -34.71 |
| Std. Dev. (F) | | | | | | |

Muscle Activity

| | Thigh | | | | | Shank | | | |
|---|---|---|---|---|---|---|---|---|---|
| | RF | VL | VM | BF | Co-act | TA | GL | SO | Co-act |
| TDC | 0.18 | 0.20 | 0.17 | 0.00 | 54.85% | 0.00 | 0.02 | 0.17 | 19.07% |
| 45 | 0.10 | 0.01 | 0.06 | 0.00 | 17.02% | 0.09 | 0.12 | 0.01 | 12.73% |
| 60 | 0.10 | 0.01 | 0.04 | 0.00 | 15.20% | 0.00 | 0.14 | 0.01 | 15.42% |
| 90 | 0.18 | 0.31 | 0.07 | 0.02 | 55.84% | 0.08 | 0.07 | 0.26 | 23.26% |
| 120 | 0.08 | 0.23 | 0.13 | 0.01 | 43.82% | 0.07 | 0.06 | 0.19 | 27.83% |
| BDC | 0.00 | 0.00 | 0.09 | 0.01 | 8.89% | 0.10 | 0.14 | 0.00 | 65.96% |

| Joint angle | Ankle | | Knee | | Hip | |
|---|---|---|---|---|---|---|
| | Inver/ever | Plan/dorsi-flexion | Fle/Ext | Abd/add | Fle/Ext | Abd/add | Exte. rot. |
| TDC | 24.31 | -18.58 | 118.62 | | 78.34 | 25.60 | 7.56 |
| 45 | 23.27 | -18.73 | 103.38 | | 76.81 | 23.83 | 11.89 |
| 60 | 22.61 | -16.48 | 95.85 | | 72.54 | 23.11 | 14.17 |
| 90 | 21.59 | -15.53 | 84.18 | | 64.40 | 21.56 | 17.23 |
| 120 | 18.89 | -17.36 | 63.09 | | 46.70 | 17.16 | 20.87 |
| BDC | 19.02 | -19.88 | 52.84 | | 30.08 | 15.59 | 23.32 |
| Std. Dev. (F) | | | | | | | |

| Coordination (%) | Normal speed | More speed ASAP | After faster speed | Prescription | Coordination always high |
|---|---|---|---|---|---|
| Thigh | 6-33 | 8-55 | | | |
| Shank | 6-89 | 12-65 | | | |

FIG.7

METHOD AND SYSTEM FOR DETERMINING DATA ASSOCIATED WITH LOWER LIMB ACTIVITY

CROSS-REFERENCE TO RELATED APPLICATION

This application claims priority of Taiwanese Patent Application No. 106107500, filed on Mar. 8, 2017.

FIELD

The disclosure relates to a method and a system for determining data associated with human activity, and more particularly to a method and a system for determining data associated with lower limb activity of a cyclist.

BACKGROUND

A conventional method of diagnosing sports injuries caused by poor posture during cycling is usually assisted by techniques of X-ray imaging or palpation. However, the conventional method may be inapplicable when a cyclist is in activity, and is lacking in terms of providing information associated with muscle activities of the cyclist. Moreover, the conventional method is usually implemented as a post-injury treatment and may be ineffective in preventing sports injuries caused by poor posture when cycling.

SUMMARY

Therefore, an object of the disclosure is to provide a method and a system for determining data associated with lower limb activity of a cyclist that can alleviate at least one of the drawbacks of the prior art.

According to one aspect of the disclosure, the method includes steps of:

a) measuring, by a joint angle measuring device in a preset duration, a variation in joint angle of a knee of the cyclist so as to obtain joint angle data that includes a result of measurement of the variation in joint angle of the knee of the cyclist as the cyclist has ridden a cycle for the preset duration;

b) sensing in the preset duration, by a force sensing device disposed on the cycle, at least one of torque applied on a crank of the cycle or pedaling force applied to a pedal of the cycle so as to obtain force data that is associated with lower limb force of the cyclist;

c) measuring, by a rotation measuring device, an angular position of the crank with respect to a reference point of the cycle in the preset duration so as to obtain crank angle data;

d) measuring, by a surface electromyography (EMG) measuring device in the preset duration, a variation in an electrical potential of at least one measured muscle selected from a plurality of lower limb muscles of the cyclist so as to generate a measured EMG signal;

e) digitalizing, by a digitalizing device, the joint angle data, the force data, the crank angle data and the measured EMG signal, and outputting, by the digitalizing device, the joint angle data, the force data, the crank angle data and the measured EMG signal thus digitalized to a signal processing device;

f) estimating, by the signal processing device which is executing a musculoskeletal simulation module thereof, plural entries of activation data that is associated respectively with the lower limb muscles of the cyclist, and joint moment data that is associated with joint moment of the knee of the cyclist based on the joint angle data, the force data and the crank angle data thus digitalized, and based on characteristics data that is associated with a gender, body weight and body height of the cyclist;

g) converting, by the signal processing device which is executing the musculoskeletal simulation module, the entries of activation data corresponding respectively to the lower limb muscles other than the at least one measured muscle into estimated EMG signals based on the measured EMG signal thus digitalized and the entry of activation data corresponding to the at least one measured muscle; and h) computing, by the signal processing device which is executing a data analysis module, a coactivation parameter associated with muscle coactivation of the lower limb muscles of the cyclist based on the measured EMG signal thus digitalized and the estimated EMG signals.

According to another aspect of the disclosure, the system includes a cycle, a joint angle measuring device, a force sensing device, a rotation measuring device, a surface EMG measuring device, a digitalizing device and a signal processing device.

The cycle is disposed on a trainer rack and is configured to be ridden by a cyclist for a preset duration.

The joint angle measuring device is configured to measure, in the preset duration, a variation in joint angle of a knee of the cyclist so as to obtain joint angle data that includes a result of measurement of the variation in joint angle of the knee of the cyclist as the cyclist has ridden a cycle for the preset duration.

The force sensing device is disposed on the cycle and is configured to sense, in the preset duration, at least one of torque applied on a crank of the cycle or pedaling force applied to a pedal of the cycle so as to obtain force data that is associated with lower limb force of the cyclist.

The rotation measuring device is configured to measure an angular position of the crank with respect to a reference point of the cycle in the preset duration so as to obtain crank angle data.

The surface EMG measuring device is configured to measure, in the preset duration, a variation in an electrical potential of at least one measured muscle selected from a plurality of lower limb muscles of the cyclist so as to generate a measured EMG signal.

The digitalizing device is configured to digitalize the joint angle data, the force data, the crank angle data and the measured EMG signal, and to output the joint angle data, the force data, the crank angle data and the measured EMG signal thus digitalized.

The signal processing device is electrically connected to the digitalizing device so as to receive the joint angle data, the force data, the crank angle data and the measured EMG signal thus digitalized therefrom, and includes a musculoskeletal simulation module and a data analysis module. The signal processing device is configured to execute the musculoskeletal simulation module thereof so as to estimate plural entries of activation data that is associated respectively with the lower limb muscles of the cyclist, and joint moment data that is associated with joint moment of the knee of the cyclist based on the joint angle data, the force data and the crank angle data thus digitalized, and based on characteristics data that is associated with a gender, body weight and body height of the cyclist, and to convert the entries of activation data corresponding respectively to the lower limb muscles other than the at least one measured muscle into estimated EMG signals based on the measured EMG signal thus digitalized and the entry of activation data corresponding to the at least one measured muscle. The signal processing device is further configured to execute the data analysis module thereof so as to compute a coactivation parameter associated with muscle coactivation of the lower limb muscles of the cyclist based on the measured EMG signal thus digitalized and the estimated EMG signals.

BRIEF DESCRIPTION OF THE DRAWINGS

Other features and advantages of the disclosure will become apparent in the following detailed description of the embodiments with reference to the accompanying drawings, of which:

FIG. 7 is a table illustrating an embodiment of a result report outputted by the method according to the disclosure.

DETAILED DESCRIPTION

Figure 1:
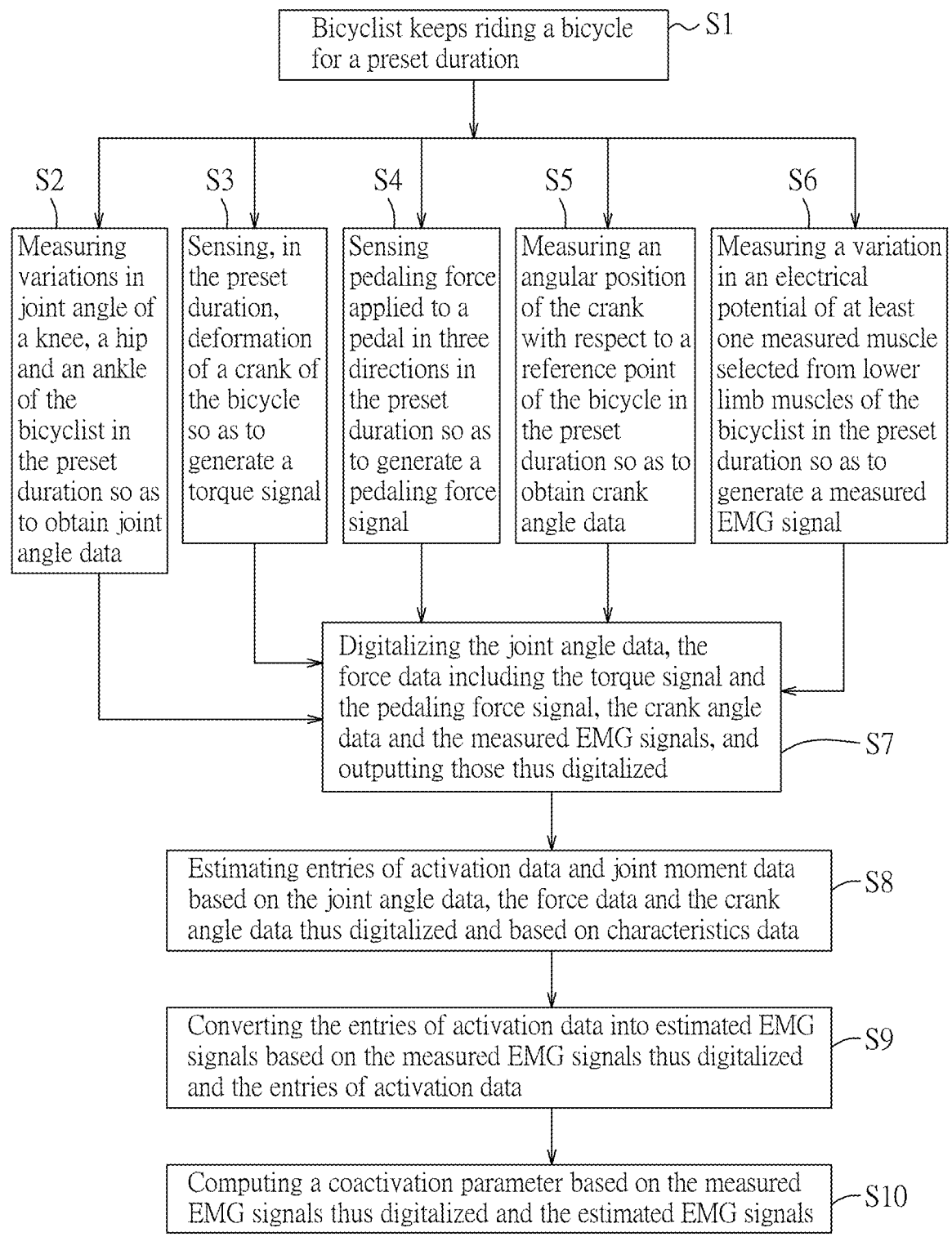
FIG. 1 is a flow diagram illustrating an embodiment of a method for determining data associated with lower limb activity of a cyclist according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
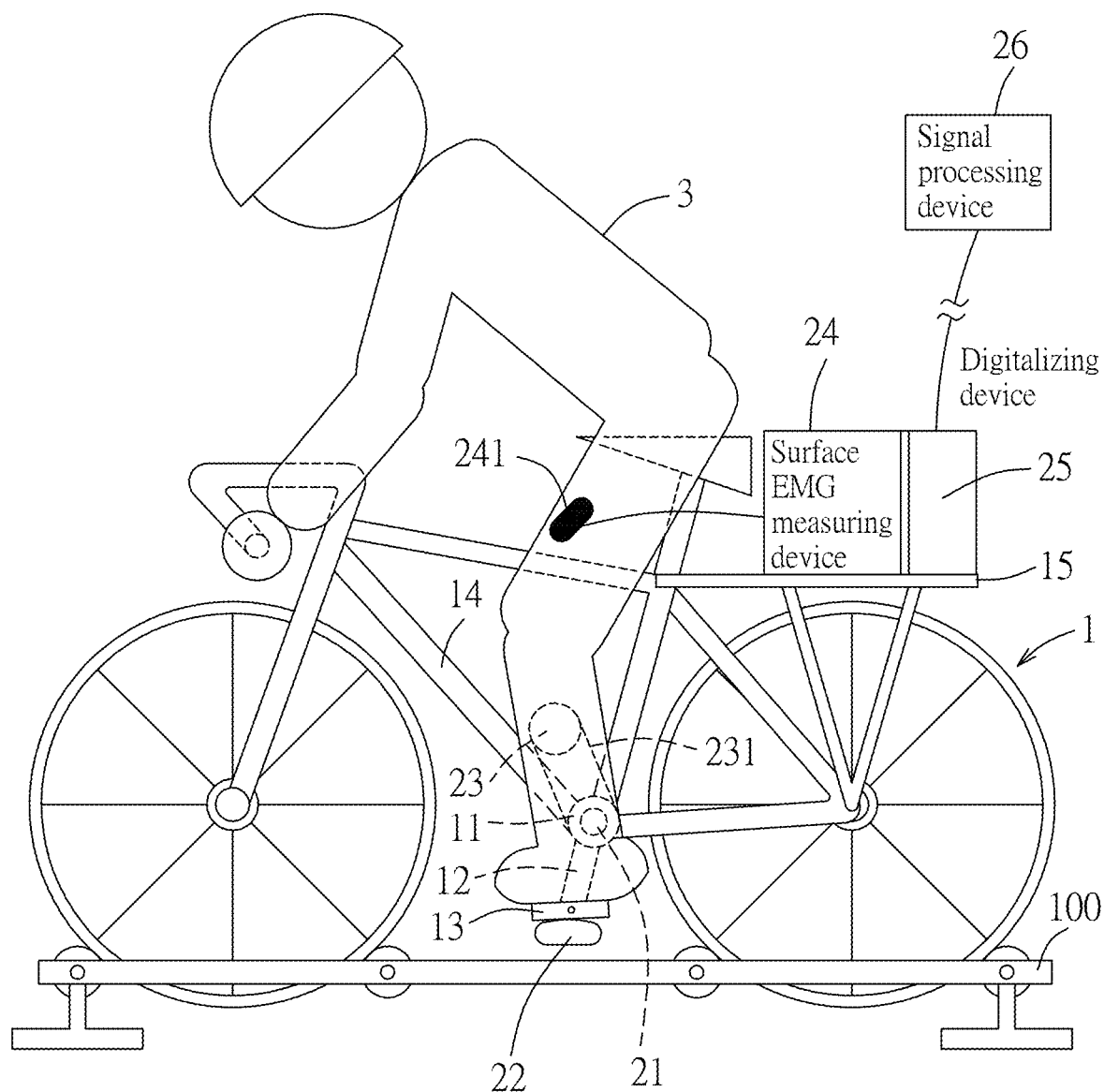
FIG. 2 is a schematic diagram illustrating an embodiment of a system for determining data associated with lower limb activity of a cyclist according to the disclosure.
Figure 3:
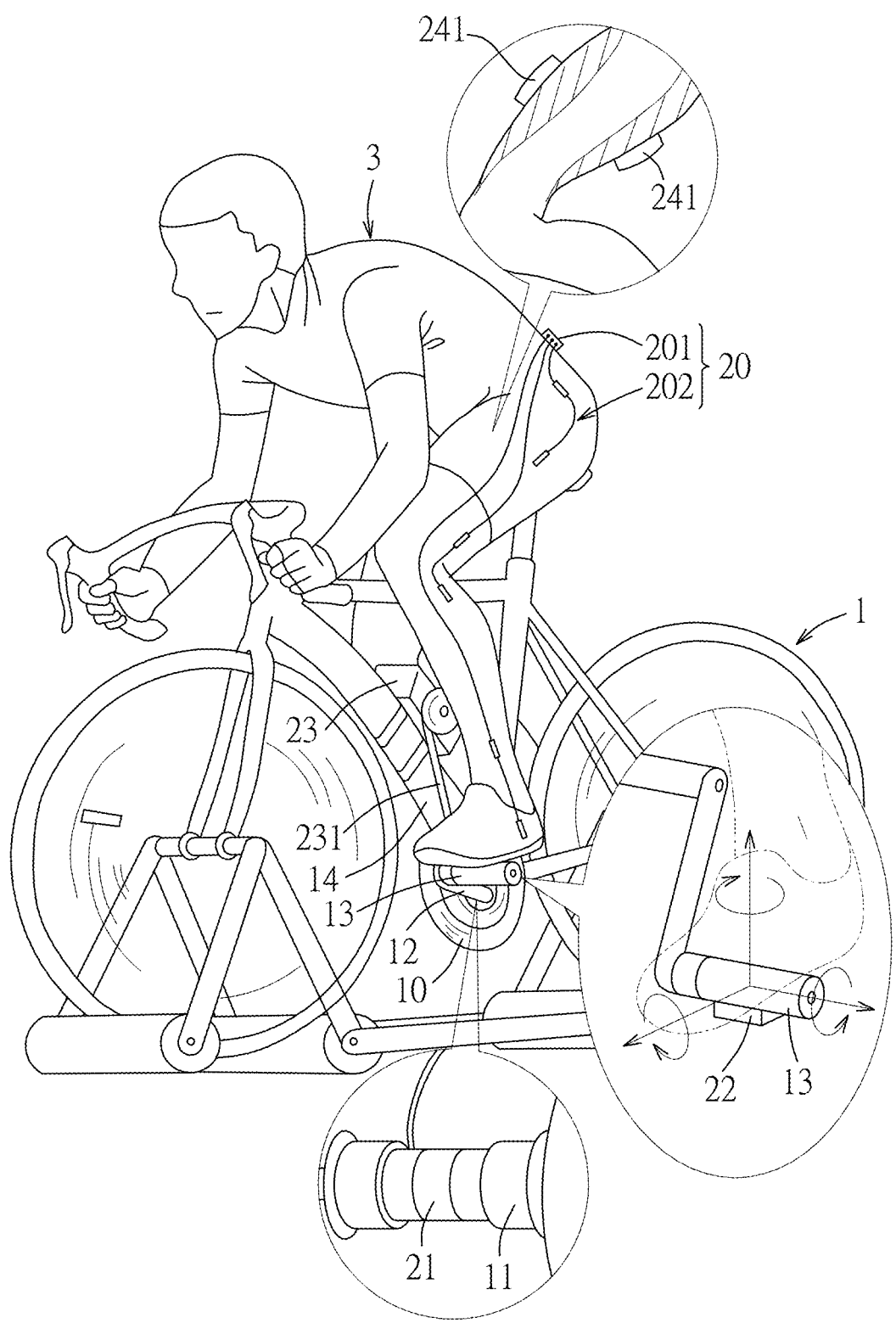
FIG. 3 is another schematic diagram illustrating the embodiment of the system according to the disclosure.
Figure 4:
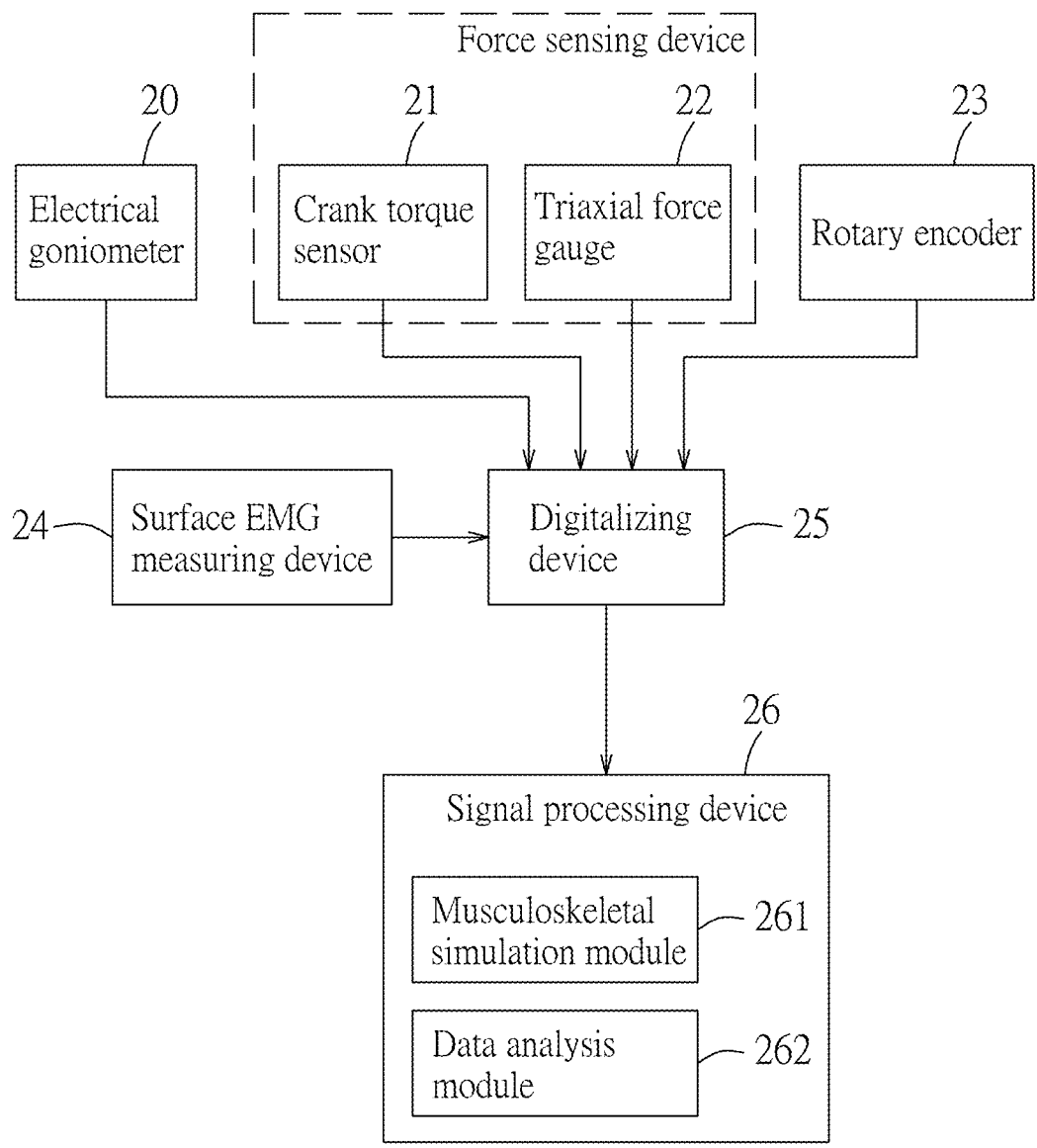
FIG. 4 is a block diagram illustrating the embodiment of the system according to the disclosure.

Referring to FIGS. 2-4, a system for determining data associated with lower limb activity of a cyclist 3 according to this disclosure is illustrated. The system includes a cycle 1 that is disposed on a trainer rack 100 and that is configured to be ridden by the cyclist 3 for a preset duration. The system further includes a joint angle measuring device, a force sensing device, a rotation measuring device, a surface electromyography (EMG) measuring device 24, a digitalizing device 25 and a signal processing device 26.

In this embodiment, the cycle 1 is implemented by a bicycle, but implementation of the cycle 1 is not limited thereto. For example, the cycle 1 may be implemented by a unicycle or a tricycle in other embodiments.

In this embodiment, the joint angle measuring device is implemented by an electrical goniometer 20 available from Biometrics Ltd. The electrical goniometer 20 includes a host processor 201 and a plurality of sensors 202 (only one is labeled in FIG. 3) that are connected to the host processor 201. The plurality of sensors 202 are disposed adjacent to a knee, a hip and an ankle of the cyclist 3. The plurality of sensors 202 are configured to, as the cyclist 3 rides the cycle 1 for the preset duration, measure, during a time period which lasts the preset duration in which the cyclist 3 rides the cycle 1, a variation in joint angle of the knee, a variation in joint angle of the hip, and a variation in joint angle of the ankle of the cyclist 3 in a three-dimensional (3-D) space, so as to obtain joint angle data that includes a result of measurement of the variation in joint angle of the knee, the variation in joint angle of the hip, and the variation in joint angle of the ankle of the cyclist 3. Thereafter, the joint angle data is outputted to the host processor 201, such that the host processor 201 receives the joint angle data outputted by the plurality of sensors 202. However, implementation of the joint angle measuring device may vary in other embodiments, and is not limited to what is disclosed herein. For example, the joint angle measuring device may be implemented by an inertial measurement device.

The force sensing device is disposed on the cycle 1 and is configured to sense, during the time period, at least one of torque applied on a crank 12 of the cycle 1 or pedaling force applied to a pedal 13 of the cycle 1 so as to obtain force data that is associated with lower limb force of the cyclist 3. In this embodiment, the force sensing device includes a crank torque sensor 21 and/or a triaxial force gauge 22. The crank torque sensor 21 may be disposed at a bottom bracket 11 of the cycle 1, or may be disposed on a crankset of the cycle 1. The crank torque sensor 21 is configured to sense deformation of the crank 12 of the cycle 1 caused by the pedaling force applied to the pedal 13 which is connected to the crank 12 during the time period so as to generate a torque signal associated with the torque applied on the crank 12. The triaxial force gauge 22 is disposed on a surface of the pedal 13, and is configured to sense the pedaling force applied to the pedal 13 during the time period so as to generate a pedaling force signal. The force data includes the torque signal and/or the pedaling force signal. In a variant of this embodiment where the force sensing device includes merely one of the crank torque sensor 21 and the triaxial force gauge 22, the system obtains a corresponding one of the torque signal and the pedaling force signal, and the other one of the torque signal and the pedaling force signal is deduced from what has been obtained. However, implementation of the force sensing device may vary in other embodiments, and is not limited to what are disclosed herein.

The rotation measuring device is configured to measure an angular position of the crank 12 with respect to a reference point, e.g., the top dead center (TDC), of the cycle 1 during the time period so as to obtain crank angle data. In this embodiment, the rotation measuring device is implemented by a rotary encoder 23 (e.g., an E6F-AB3C-C absolute rotary encoder with BCD encoded output that is available from OMRON corporation in Kyoto, Japan). The rotary encoder 23 is disposed on a down tube 14 of the cycle 1, and is coupled via a belt 231 to a chainring 10 of the cycle 1 which is co-rotatable with the crank 12. The rotary encoder 23 is configured to measure the angular position of the crank 12 at time instances during the time period. However, implementation of the rotation measuring device may vary in other embodiments, and is not limited to what is disclosed herein. For example, the rotation measuring device may be implemented to measure the angular position of the crank 12 by means of photography.

Figure 5:
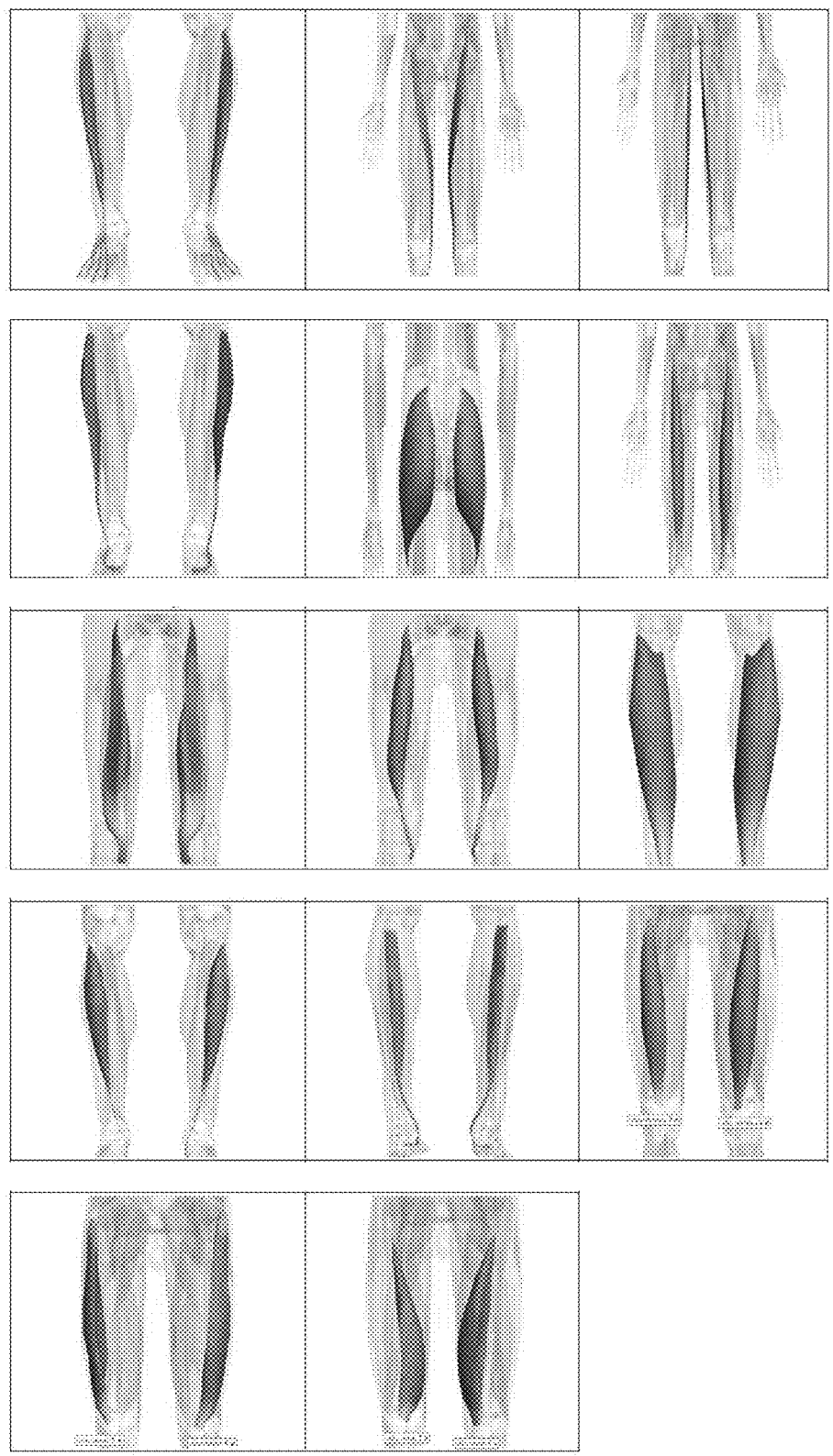
FIG. 5 is a schematic diagram illustrating fourteen pairs of lower limb muscles adjacent to two knees.

The surface EMG measuring device 24 is configured to measure, via electrode pads 241 thereof that are disposed on the skin of the lower limb of the cyclist 3, a variation in an electrical potential of at least one measured muscle selected from a plurality of lower limb muscles of the cyclist 3 (two measured muscles are given as an example in this embodiment) during the time period so as to generate a measured EMG signal. In this embodiment, the surface EMG measuring device 24 is disposed at a rear rack 15 of the cycle 1. The surface EMG measuring device 24 is configured to measure, at a sampling rate equal to one thousand Hz, the variation in the electrical potential of each of the two measured muscles that are near the skin of an identical lower limb (e.g., two superficial muscles of a left thigh) of the cyclist 3 with respect to a base electrical potential obtained by one of the electrode pads 241 (there are totally two electrode pads 241 in this embodiment) disposed adjacent to a head of a fibula of the cyclist 3 for reduction of noise from skin. The two measured muscles are two of fourteen muscles near a knee of a lower limb as shown in FIG. 5. Implementation of obtaining information about the remaining twelve muscles will be described later. It has been known that sports injuries caused by poor posture during cycling are mainly knee injuries. Analyzing coactivation of the fourteen muscles adjacent to the knee of the lower limb by the method and the system of this disclosure may facilitate diagnosis of knee injuries.

The digitalizing device 25 is electrically connected to the joint angle measuring device (e.g., the electrical goniometer 20), the force sensing device (e.g., the crank torque sensor 21 and/or the triaxial force gauge 22), the rotation measuring device (e.g., the rotary encoder 23), and the surface EMG measuring device 24 for receiving respectively the joint angle data, the force data (including the torque signal and/or the pedaling force signal), the crank angle data and the measured EMG signal therefrom at an acquisition rate (e.g., one thousand Hz). The digitalizing device 25 is configured to amplify and digitalize the joint angle data, the force data, the crank angle data and the measured EMG signal thus received, and to output those thus amplified and digitalized (also referred to hereinafter as "digitalized versions" of these data/signal). In this embodiment, the digitalizing device 25 is implemented by an MP150 data acquisition and analysis system available from BIOPAC Systems Incorporated. The digitalizing device 25 is disposed on the rear rack 15 of the cycle 1. Moreover, the digitalizing device 25 is configured to record the digitalized versions of the joint angle data, the force data, the crank angle data and the measured EMG signal.

The signal processing device 26 is electrically connected to the digitalizing device 25 so as to receive the digitalized versions of the joint angle data, the force data, the crank angle data and the measured EMG signal therefrom. In this embodiment, the signal processing device 26 may be implemented by a personal computer or by a notebook computer, but is not limited thereto. The signal processing device 26 includes a musculoskeletal simulation module 261 and a data analysis module 262. The musculoskeletal simulation module 261 may be implemented by a musculoskeletal simulation software tool, such as OpenSim or AnyBody. The data analysis module 262 may be implemented by a data analysis software tool, such as Labview. However, implementations of the musculoskeletal simulation module 261 and the data analysis module 262 are not limited to what are disclosed herein, and may vary in other embodiments.

The signal processing device 26 is configured to execute the musculoskeletal simulation module 261 thereof so as to estimate plural entries of activation data that are associated respectively with the lower limb muscles of the cyclist 3, and joint moment data that is associated with joint moment of the knee, joint moment of the hip and joint moment of the ankle of the cyclist 3, based on the digitalized versions of the joint angle data, the force data and the crank angle data, and based on characteristics data that may be obtained in advance and that is associated with gender, body weight and body height of the cyclist 3.

In addition, the signal processing device 26 is further configured to execute the musculoskeletal simulation module 261 thereof so as to convert the entries of activation data corresponding respectively to the lower limb muscles other than the two measured muscles (i.e., the remaining twelve muscles) into estimated EMG signals based on the digitalized version of the measured EMG signal and the entries of activation data corresponding to the two measured muscles.

In one embodiment, the signal processing device 26 is configured to execute the musculoskeletal simulation module 261 so as to normalize the digitalized version of the measured EMG signal based on isometric maximal voluntary contraction (iMVC) and to convert the entries of activation data corresponding respectively to the lower limb muscles other than the two measured muscles into the estimated EMG signals based on the digitalized version of the measured EMG signal thus normalized (also referred to hereinafter as "normalized version" of the measured EMG signal).

Moreover, the signal processing device 26 is configured to execute the data analysis module 262 thereof so as to compute at least one coactivation parameter associated with muscle coactivation of the lower limb muscles of the cyclist 3 based on the digitalized version of the measured EMG signal and the estimated EMG signals. The coactivation parameter of the lower limb muscles of the cyclist 3 is computed based on a formula of $$\text{Coactivation} = \frac{\int \min\{EMGa, EMGb\}dt}{\int \max\{EMGa, EMGb\}dt},$$

where Coactivation is the coactivation parameter, and EMGa and EMGb are two EMG signals selected from EMG signals of the fourteen muscles adjacent to the knee of the lower limb, including the digitalized version of the measured EMG signal and the estimated EMG signals.

Referring to FIG. 1, an embodiment of a method for determining data associated with lower limb activity of the cyclist 3 according to this disclosure is illustrated. The method is to be implemented by the system that is previously mentioned. The method includes the following steps S1-S10.

In step S1, the cyclist 3 is requested to keep riding the cycle 1 for the preset duration (e.g., five minutes, ten minutes, thirty minutes, or the like). However, in some embodiments, the cyclist 3 may be requested to keep riding the cycle 1 for a predetermined distance (e.g., one kilometer) or a predetermined number of pedaling cycles (e.g., one hundred pedaling cycles).

Figure 6:
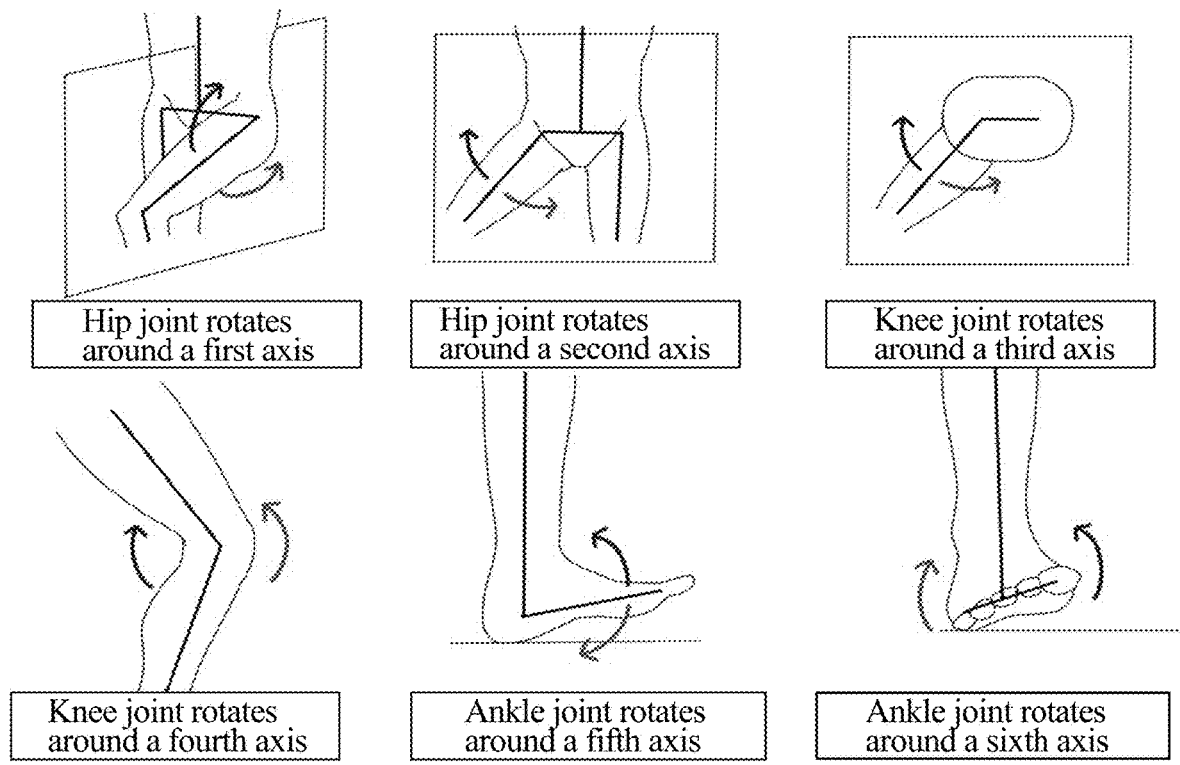
FIG. 6 is a schematic diagram illustrating respective ways of movements of a hip joint, a knee joint and an ankle joint of a cyclist.

In step S2, the joint angle measuring device, which is implemented by the electrical goniometer 20 in this embodiment, measures the variation in joint angle of the knee, the variation in joint angle of the hip, and the variation in joint angle of the ankle of the cyclist 3 as shown in FIG. 6 during a time period which lasts the preset duration and during which the cyclist 3 rides the cycle 1, so as to obtain the joint angle data as the cyclist 3 rides the cycle 1. Thereafter, the joint angle data is outputted to the digitalizing device 25.

At the same time, the force sensing device disposed on the cycle 1 senses, during the time period, at least one of the torque applied on the crank 12 of the cycle 1 or pedaling force applied to the pedal 13 of the cycle 1, so as to obtain the force data that is associated with the lower limb force of the cyclist 3. Specifically speaking, in step S3, the crank torque sensor 21 senses, during the time period, the deformation of the crank 12 of the cycle 1 that is caused by the pedaling force applied to the pedal 13 so as to generate the torque signal. In step S4, the triaxial force gauge 22 senses the pedaling force applied to the pedal 13 in three directions as shown in FIG. 3 during the time period so as to generate the pedaling force signal. The force data includes the torque signal and the pedaling force signal.

In step S5, the rotation measuring device, which is implemented by the rotary encoder 23, measures the angular position of the crank 12 with respect to the reference point of the cycle 1 during the time period so as to obtain the crank angle data.

In step S6, the surface EMG measuring device 24 measures the variation in the electrical potential of at least one measured muscle selected from the plurality of lower limb muscles of the cyclist 3 during the time period so as to generate the measured EMG signal. In this embodiment, two measured muscles selected from the plurality of lower limb muscles of the cyclist 3 are measured by the surface EMG measuring device 24, and two measured EMG signals are thus generated. Specifically speaking, the surface EMG measuring device 24 measures, via the electrode pads 241 disposed to the left thigh of the cyclist 3, at the sampling rate equal to one thousand Hz, the variation in the electrical potential of each of two measured muscles at the identical lower limb of the cyclist 3 with respect to the base electrical potential obtained by one of the electrode pads 241 disposed adjacent to the head of the fibula for noise reduction. It should be noted that in other embodiments, the variation in the electrical potential of each of two measured muscles at two different lower limbs may be measured.

In step S7, the digitalizing device 25 receives the joint angle data, the force data, which includes the torque signal and the pedaling force signal, the crank angle data and the measured EMG signals at the acquisition rate equal to one thousand Hz. The digitalizing device 25 amplifies and digitalizes the joint angle data, the force data, the crank angle data and the measured EMG signals thus received, and records the joint angle data, the force data, the crank angle data and the measured EMG signals thus amplified and digitalized. The digitalizing device 25 outputs, via a wire or wirelessly, the joint angle data, the force data, the crank angle data and the measured EMG signals thus amplified and digitalized to the signal processing device 26.

In step S8, the signal processing device 26 executes the musculoskeletal simulation module 261 thereof to estimate plural entries of activation data that are associated respectively with the fourteen lower limb muscles adjacent to the knee of the cyclist 3, and the joint moment data that is associated with the joint moment of the knee, the joint moment of the hip, and the joint moment of the ankle of the cyclist 3 based on the joint angle data, the force data and the crank angle data thus amplified and digitalized, and based on the characteristics data that is associated with the gender, the body weight and the body height of the cyclist 3. In this embodiment, each of the entries of activation data is implemented to be a value between zero and one. Specifically speaking, the joint angle data thus amplified and digitalized enables the musculoskeletal simulation module 261 to estimate the entries of activation data and the joint moment data. The entries of activation data and the joint moment data are subsequently refined according to the force data and the crank angle data thus amplified and digitalized, so that the entries of activation data and the joint moment data are faithfully estimated. It should be noted that the entries of activation data and the joint moment data thus estimated are correlated, and they can faithfully reflect activities of the lower limb(s) of the cyclist 3. Since implementation of estimating the entries of activation data and the joint moment data are well known to one skilled in the relevant art, details thereof will be omitted herein for the sake of brevity.

In step S9, the signal processing device 26 which is executing the musculoskeletal simulation module 261 converts the entries of activation data corresponding respectively to the lower limb muscles other than the two measured muscles into estimated EMG signals based on the measured EMG signals thus amplified and digitalized and based on the entries of activation data corresponding to the two measured muscles.

In one embodiment, the signal processing device 26 executes the musculoskeletal simulation module 261 to normalize the measured EMG signals thus amplified and digitalized and outputted by the digitalizing device 25 based on iMVC for subsequent conversion of the entries of activation data of the remaining twelve muscles. Since implementation of iMVC should be well known to one skilled in the relevant art, details thereof will be omitted herein for the sake of brevity. For further details, please refer to publications such as "The effect of pedaling rate on coordination in cycling" authored by Neptune, Kautz et al. in 1997 or "Muscle activation during cycling at different cadences: effect of maximal strength capacity" authored by Bieuzen, Lepers et al. in 2007. The signal processing device 26 then executes the musculoskeletal simulation module 261 to convert the entries of activation data corresponding respectively to the lower limb muscles other than the two measured muscles (i.e., the remaining twelve muscles of the left thigh) into the estimated EMG signals based on the measured EMG signals thus amplified, digitalized and normalized. For example, assuming that two entries of activation data associated with two lower limb muscles of the cyclist 3 are respectively 0.3 and 0.5, and that the corresponding measured EMG signals are respectively 60 mV and 100 mV, the estimated EMG signals associated with the lower limb muscles other than the two measured muscles can be determined by executing the musculoskeletal simulation module 261 based on a proportional relationship between the two entries of activation data and the two measured EMG signals.

It is worth noting that conventionally, some of the fourteen lower limb muscles adjacent to the knee are located too deep to be measured by electrode pads disposed on the skin of the lower limb, and can only be invasively measured by probes. However, by the method of this disclosure, only two superficial muscles of the cyclist 3 are required (it is possible to require only one measured muscle in some embodiments) to be non-invasively measured by the surface EMG measuring device 24 to generate respectively the two measured EMG signals. The two measured EMG signals enable the musculoskeletal simulation module 261 to generate the estimated EMG signals associated respectively with the lower limb muscles other than the two superficial muscles based on the activation data thus estimated and the two measured EMG signals. In this way, EMG signals of all of the lower limb muscles of the cyclist 3 may be either measured or estimated in a non-invasive manner.

In step S10, the signal processing device 26 which is executing the data analysis module 262 computes the coactivation parameter associated with the muscle coactivation of the lower limb muscles of the cyclist 3 based on the measured EMG signals thus amplified and digitalized and the estimated EMG signals with reference to the aforementioned formula of $$\text{Coactivation} = \frac{\int \min\{EMGa,\ EMGb\}dt}{\int \max\{EMGa,\ EMGb\}dt}.$$

Since implementation of computing the coactivation parameter is already well known to one skilled in the relevant art, detailed explanation of the same is omitted herein for the sake of brevity.

The data analysis module 262 is programmed to generate a result report as shown in FIG. 7 based on the joint moment data and the coactivation parameter(s) of the lower limb muscles of the cyclist 3. The result report includes joint moments of the hip, the knee and the ankle at different angular positions of the crank 12, joint angles of the hip, the knee and the ankle corresponding to different angular positions of the crank 12, the entries of activation data that correspond to the lower limb muscles in the thigh adjacent to the knee, which includes vastus lateralis (VL), vastus medius (VM), rectus femoris (RF), and biceps femoris-longus (BF-long), at different angular positions of the crank 12, the coactivation parameters (denoted as Co-act in FIG. 7) associated with VL, VM, RF and BF-long, the entries of activation data that correspond to the lower limb muscles in the shank adjacent to the knee, which includes gastrocnemius lateralis (GL), soleus (SO) and tibialis anterior (TA), and the coactivation parameters associated with GL, SO and TA.

According to concepts of anatomy, joints of the hip, the knee and the ankle are joints with multiple muscles nearby, so values of the coactivation parameters of the lower limb muscles adjacent to the knee (as well as the hip and the ankle) can be utilized to represent stability of the joint of the knee. Consequently, one who is skilled in the art of the musculoskeletal system, such as a sports coach or a healthcare professional, may diagnose the cyclist 3 based on the coactivation parameters and the joint moments of the hip, the knee and the ankle corresponding to different angular positions of the crank 12, and may make determinations as to whether the cyclist 3 exerts force properly during cycling, whether muscles of the cyclist 3 coordinate properly, and whether joints of the cyclist 3 are excessively loaded. Moreover, locations and causes of sports injuries may be accordingly found. For example, assuming that the joint moment of a knee corresponding to a certain angular position of the crank should have a positive value for a normal person, when it is found that a value of the joint moment of the knee corresponding to the same angular position of the crank included in the result report for the cyclist 3 is negative, the cyclist 3 will be diagnosed as having sports injuries in related muscles. Furthermore, to investigate causes of the sports injuries, the coactivation parameters included in the result report can be utilized to determine whether joints are stable and to determine whether some joints are injured. A smaller value of a coactivation parameter represents that a corresponding joint is stabler, and a greater value of a coactivation parameter represents that a corresponding joint is less stable. When it is determined that some muscles or some joints of the cyclist 3 are injured due to poor posture, the cyclist 3 may improve his/her posture or adjust cycle fitting, such as changing frame size of the cycle 1 or replacing the crank 12 or the pedal 13 thereof. In this way, chances of having sports injuries due to cycling may be reduced.

In summary, the system and the method of this disclosure measure variations in joint angles of the lower limb of the cyclist 3 to obtain the joint angle data which enables the system to execute the musculoskeletal simulation module 261 to estimate the activation data associated with the lower limb muscles (i.e., the fourteen muscles adjacent to the knee) and the joint moment data of the cyclist 3. As a result, computational complexity of musculoskeletal simulation assisted by the system and the method of this disclosure may be reduced compared with a conventional marker-based approach, and a time-consuming process of establishing markers on a test subject may be alleviated. The torque signal, the pedaling force signal and the crank angle data are utilized to refine the activation data and the joint moment data so that activation data and joint moment data in actual activities can be faithfully estimated. Furthermore, only two measured muscles of the cyclist 3 are required to be measured by the surface EMG measuring device 24 to generate respectively the two measured EMG signals which enable the musculoskeletal simulation module 261 to generate estimated EMG signals associated respectively with the lower limb muscles other than the two measured muscles based on the activation data thus estimated and the two measured EMG signals. In this way, it is not required to measure EMG signals of all of the lower limb muscles of the cyclist 3. The data analysis module 262 computes the coactivation parameters associated with the fourteen lower limb muscles based on the estimated EMG signals and the measured EMG signals, and outputs the result report including the joint moment data and the coactivation parameters so as to provide information regarding the joint moment of the knee, the joint moment of the hip and the joint moment of the ankle of the cyclist 3 and situations of the muscle coactivation of the lower limb muscles thereof. Consequently, sports injuries caused by poor posture of cycling may be diagnosed based on the result report thus outputted.

It should be noted herein that the evaluation/determination performed by the method and system of this disclosure are equally applicable for a rider of a unicycle, a tricycle, or the like, as would be appreciated by those skilled in the art.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for determining data associated with lower limb activity of a cyclist to facilitate diagnosing the cyclist, comprising steps of:
    a) measuring, by a joint angle measuring device during a time period having a preset duration, a variation in joint angle of a knee of the cyclist so as to obtain joint angle data that includes a result of measurement of the variation in joint angle of the knee of the cyclist as the cyclist rides a cycle for the preset duration;

b) sensing, during the time period, by a force sensing device disposed on the cycle, at least one of torque applied on a crank of the cycle or pedaling force applied to a pedal of the cycle so as to obtain force data that is associated with lower limb force of the cyclist;

c) measuring, by a rotation measuring device, an angular position of the crank with respect to a reference point of the cycle during the time period so as to obtain crank angle data;

d) measuring, by a surface electromyography (EMG) measuring device during the time period, a variation in an electrical potential of at least one measured muscle selected from a plurality of lower limb muscles of the cyclist so as to generate a measured EMG signal, where the at least one measured muscle is more assessable than the lower limb muscles other than the at least one measured muscle;

e) digitalizing, by a digitalizing device, the joint angle data, the force data, the crank angle data and the measured EMG signal, and outputting, by the digitalizing device, the joint angle data, the force data, the crank angle data and the measured EMG signal thus digitalized to a signal processing device;

f) estimating, by the signal processing device which is executing a musculoskeletal simulation module thereof, plural entries of activation data that are associated respectively with the lower limb muscles of the cyclist, and joint moment data that is associated with joint moment of the knee of the cyclist based on the joint angle data, the force data and the crank angle data thus digitalized, and based further on characteristics data that is associated with gender, body weight and body height of the cyclist, the entries of activation data and the joint moment data thus estimated being correlated;

g) converting, by the signal processing device which is executing the musculoskeletal simulation module, those of the entries of activation data corresponding respectively to the lower limb muscles other than the at least one measured muscle into estimated EMG signals which are estimation of variations in electrical potentials respectively of the lower limb muscles other than the at least one measured muscle based on the measured EMG signal thus digitalized and at least one of the entries of activation data corresponding to the at least one measured muscle;

h) computing, by the signal processing device which is executing a data analysis module, a coactivation parameter associated with muscle coactivation of the lower limb muscles of the cyclist based on the measured EMG signal thus digitalized and the estimated EMG signals; and i) generating, by the signal processing device which is executing the data analysis module, a result report based on the joint moment data and the coactivation parameter, the result report for diagnosing sports injuries in the cyclist.

2. The method as claimed in claim 1, wherein step a) includes measuring, by a plurality of sensors of an electrical goniometer that are disposed adjacent to the knee of the cyclist, the variation in joint angle of the knee of the cyclist in a three-dimensional (3-D) space, the electrical goniometer serving as the joint angle measuring device.

3. The method as claimed in claim 1, the force sensing device including a crank torque sensor that is disposed on the cycle, wherein step b) includes sensing, by the crank torque sensor during the time period, deformation of the crank of the cycle that is caused by the pedaling force applied to the pedal which is connected to the crank.

4. The method as claimed in claim 1, the force sensing device including a triaxial force gauge that is disposed on the pedal, wherein step b) includes sensing, by the triaxial force gauge during the time period, the pedaling force applied to the pedal.

5. The method as claimed in claim 1, the force sensing device including a crank torque sensor that is disposed on the cycle and a triaxial force gauge that is disposed on the pedal, wherein step b) includes sensing, by the crank torque sensor during the time period, deformation of the crank of the cycle that is caused by the pedaling force applied to the pedal which is connected to the crank so as to generate a torque signal, and sensing, by the triaxial force gauge during the time period, the pedaling force applied to the pedal so as to generate a pedaling force signal, the force data including the torque signal and the pedaling force signal.

6. The method as claimed in claim 1, wherein step c) includes measuring, by a rotary encoder that serves as the rotation measuring device, that is disposed on the cycle and that is coupled to a chainring of the cycle which is co-rotatable with the crank, the angular position of the crank during the time period.

7. The method as claimed in claim 1, wherein step h) includes computing, by the signal processing device which is executing the data analysis module, the coactivation parameter of the lower limb muscles of the cyclist based on a formula of $$\text{Coactivation} = \frac{\int \min\{EMGa, EMGb\}dt}{\int \max\{EMGa, EMGb\}dt},$$

where Coactivation is the coactivation parameter, and EMGa and EMGb are two EMG signals selected from EMG signals of the lower limb muscles, including the measured EMG signal thus digitalized and the estimated EMG signals.

8. The method as claimed in claim 1, wherein step d) includes measuring, by the surface EMG measuring device at a sampling rate equal to one thousand Hz, the variation in the electrical potential of each of two measured muscles at an identical lower limb or at respective two lower limbs of the cyclist with respect to a base electrical potential obtained by an electrode pad configured to be disposed adjacent to a head of a fibula of the cyclist for noise reduction.

9. The method as claimed in claim 1, wherein step g) includes sub-steps of:

normalizing, by the signal processing device which is executing the musculoskeletal simulation module, the measured EMG signal thus digitalized based on isometric maximal voluntary contraction (iMVC); and converting, by the signal processing device which is executing the musculoskeletal simulation module, the entries of activation data corresponding respectively to the lower limb muscles other than the at least one measured muscle into the estimated EMG signals based on the measured EMG signal thus digitalized and normalized.

10. The method as claimed in claim 1, wherein:
step a) further includes measuring, by the joint angle measuring device in the preset duration, a variation in joint angle of a hip of the cyclist and a variation in joint angle of an ankle of the cyclist so as to obtain the joint angle data that further includes results of measurement of the variation in joint angle of the hip of the cyclist and the variation in joint angle of the ankle of the cyclist; and
step f) further includes estimating, by the signal processing device which is executing the musculoskeletal simulation module, joint moment data that is associated with joint moment of the hip of the cyclist and joint moment of the ankle of the cyclist based on the joint angle data, the force data and the crank angle data thus digitalized, and the characteristics data of the cyclist.

11. A system for determining data associated with lower limb activity of a cyclist to facilitate diagnosing the cyclist, comprising:
a cycle disposed on a trainer rack and configured to be ridden by a cyclist for a preset duration, said cycle including a crank and a pedal connected to said crank;
a joint angle measuring device configured to measure, during a time period which lasts the preset duration and in which the cyclist rides said cycle, a variation in joint angle of a knee of the cyclist so as to obtain joint angle data that includes a result of measurement of the variation in joint angle of the knee of the cyclist as the cyclist rides said cycle for the preset duration;
a force sensing device disposed on said cycle and configured to sense, during the time period, at least one of torque applied on said crank of said cycle or pedaling force applied to said pedal of said cycle so as to obtain force data that is associated with lower limb force of the cyclist;
a rotation measuring device configured to measure an angular position of said crank with respect to a reference point of said cycle during the time period so as to obtain crank angle data;
a surface electromyography (EMG) measuring device configured to measure, during the time period, a variation in an electrical potential of at least one measured muscle selected from a plurality of lower limb muscles of the cyclist so as to generate a measured EMG signal, where the at least one measured muscle is more assessable than the lower limb muscles other than the at least one measured muscle;
a digitalizing device configured to digitalize the joint angle data, the force data, the crank angle data and the measured EMG signal, and to output the joint angle data, the force data, the crank angle data and the measured EMG signal thus digitalized; and
a signal processing device electrically connected to said digitalizing device so as to receive the joint angle data, the force data, the crank angle data and the measured EMG signal thus digitalized therefrom, and including a musculoskeletal simulation module and a data analysis module,
wherein said signal processing device is configured to execute said musculoskeletal simulation module thereof so as to estimate plural entries of activation data that are associated respectively with the lower limb muscles of the cyclist, and joint moment data that is associated with joint moment of the knee of the cyclist based on the joint angle data, the force data and the crank angle data thus digitalized, and based further on characteristics data that is associated with gender, body weight and body height of the cyclist, the entries of activation data and the joint moment data thus estimated being correlated, and
convert those of the entries of activation data corresponding respectively to the lower limb muscles other than the at least one measured muscle into estimated EMG signals which are estimation of variations in electrical potentials respectively of the lower limb muscles other than the at least one measured muscle based on the measured EMG signal thus digitalized and at least one of the entries of activation data corresponding to the at least one measured muscle, and
wherein said signal processing device is further configured to execute said data analysis module thereof so as to compute a coactivation parameter associated with muscle coactivation of the lower limb muscles of the cyclist based on the measured EMG signal thus digitalized and the estimated EMG signals;
wherein said signal processing device is further configured to generate a result report based on the joint moment data and the coactivation parameter, the result report for diagnosing sports injuries in the cyclist.

12. The system as claimed in claim 11, wherein said joint angle measuring device is implemented by an electrical goniometer including a plurality of sensors that are disposed adjacent to the knee of the cyclist and that are configured to measure the variation in joint angle of the knee of the cyclist in a three-dimensional (3-D) space.

13. The system as claimed in claim 11, wherein said force sensing device includes a crank torque sensor that is disposed on said cycle and that is configured to sense, during the time period, deformation of said crank of said cycle caused by the pedaling force applied to said pedal.

14. The system as claimed in claim 11, wherein said force sensing device includes a triaxial force gauge that is disposed on said pedal and that is configured to sense, during the time period, the pedaling force applied to said pedal.

15. The system as claimed in claim 11, wherein said force sensing device includes:
a crank torque sensor that is disposed on said cycle and that is configured to sense, during the time period, deformation of said crank of said cycle caused by the pedaling force applied to said pedal so as to generate a torque signal; and
a triaxial force gauge that is disposed on said pedal and that is configured to sense, during the time period, the pedaling force applied to said pedal so as to generate a pedaling force signal, the force data including the torque signal and the pedaling force signal.

16. The system as claimed in claim 11, wherein said cycle further includes a chainring that is co-rotatable with said crank, and said rotation measuring device is implemented by a rotary encoder that is disposed on said cycle, that is coupled to said chainring of said cycle, and that is configured to measure the angular position of said crank in the preset duration.

17. The system as claimed in claim 11, wherein said signal processing device is configured to execute said data analysis module so as to compute the coactivation parameter of the lower limb muscles of the cyclist based on a formula of $$\text{Coactivation} = \frac{\int \min\{EMGa, EMGb\}dt}{\int \max\{EMGa, EMGb\}dt},$$

where Coactivation is the coactivation parameter, and EMGa and EMGb are two EMG signals selected from EMG signals of the lower limb muscles, including the measured EMG signal thus digitalized and the estimated EMG signals.

18. The system as claimed in claim 11, wherein said surface EMG measuring device includes an electrode pad, and is configured to measure, at a sampling rate equal to one thousand Hz, the variation in the electrical potential of each of two measured muscles at an identical lower limb or at respective two lower limbs of the cyclist with respect to a base electrical potential obtained by said electrode pad configured to be disposed adjacent to a head of a fibula of the cyclist for noise reduction.

19. The system as claimed in claim 11, wherein said signal processing device is configured to execute said musculoskeletal simulation module so as to normalize the measured EMG signal thus digitalized based on isometric maximal voluntary contraction (iMVC), and to convert those of the entries of activation data corresponding respectively to the lower limb muscles other than the at least one measured muscle into the estimated EMG signals based on the measured EMG signal thus digitalized and normalized.

20. The system as claimed in claim 11, wherein:
said joint angle measuring device is further configured to measure, during the time period, a variation in joint angle of a hip of the cyclist and a variation in joint angle of an ankle of the cyclist so as to obtain the joint angle data that further includes results of measurement of the variation in joint angle of the hip of the cyclist and the variation in joint angle of the ankle of the cyclist; and
said signal processing device is further configured to execute said musculoskeletal simulation module so as to estimate joint moment data that is further associated with joint moment of the hip of the cyclist and joint moment of the ankle of the cyclist based on the joint angle data, the force data and the crank angle data thus digitalized, and the characteristics data of the cyclist.

* * * * *